United States Patent [19]

Cruz

[11] 4,401,241
[45] Aug. 30, 1983

[54] NEBULIZER BOTTLE

[75] Inventor: Exequiel D. Cruz, Palatine, Ill.

[73] Assignee: Respiratory Care, Inc., Arlington Heights, Ill.

[21] Appl. No.: 226,087

[22] Filed: Jan. 19, 1981

[51] Int. Cl.³ .............................................. B67D 5/06
[52] U.S. Cl. ..................................... 222/527; 222/80; 128/200.21
[58] Field of Search ............... 222/526, 527, 528, 529, 222/530, 543, 548, 566, 573; 128/200.14, 200.16, 200.18, 200.21; 248/75, 79; 261/78 A, DIG. 65; 292/299

[56] References Cited

U.S. PATENT DOCUMENTS

| | | | |
|---|---|---|---|
| 3,572,660 | 3/1971 | Mahon et al. | 261/78 |
| 3,903,216 | 9/1975 | Allan et al. | 261/78 A |
| 3,915,386 | 10/1975 | Vora | 239/338 |
| 3,929,128 | 12/1975 | Pekkarinen | 128/194 |
| 4,007,238 | 2/1977 | Glenn | 261/78 A |
| 4,177,945 | 12/1979 | Schwartz et al. | 239/338 |
| 4,190,046 | 2/1980 | Virag | 128/200.21 |
| 4,236,655 | 12/1980 | Humphries | 222/465 |

Primary Examiner—Joseph J. Rolla
Assistant Examiner—Michael S. Huppert
Attorney, Agent, or Firm—Eric P. Schellin

[57] ABSTRACT

A thermoplastic bottle container has tubular inflow and outflow sections projecting from its top wall and a coupling enlargement of a tubular passage formation on the side wall to accommodate its use with other components of a nebulizing system, for inhalation therapy purposes. The coupling enlargement has frangible portions through which the puncturing end of a flexible tube is inserted for withdrawal of liquid from the bottom of the container. A latch and retainer molded integral with the container releasably holds the outflow section in a bent operative position.

10 Claims, 6 Drawing Figures

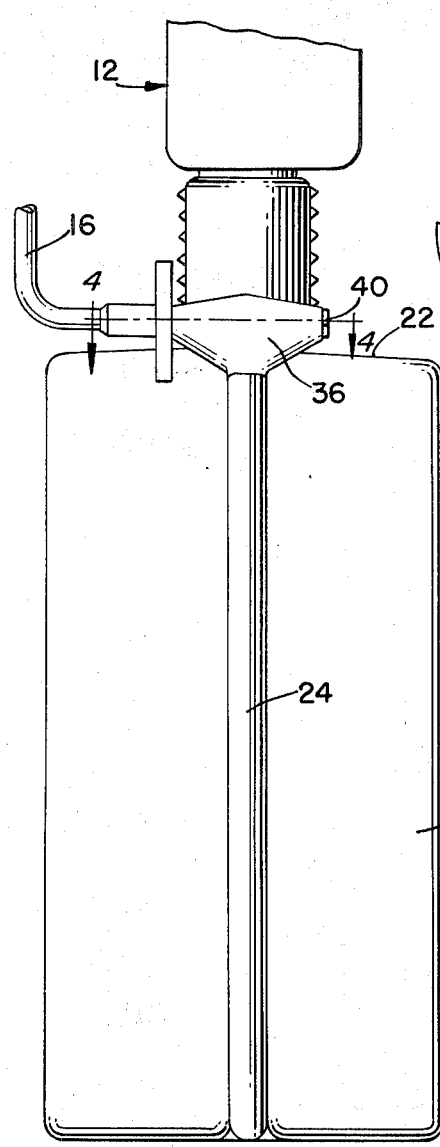
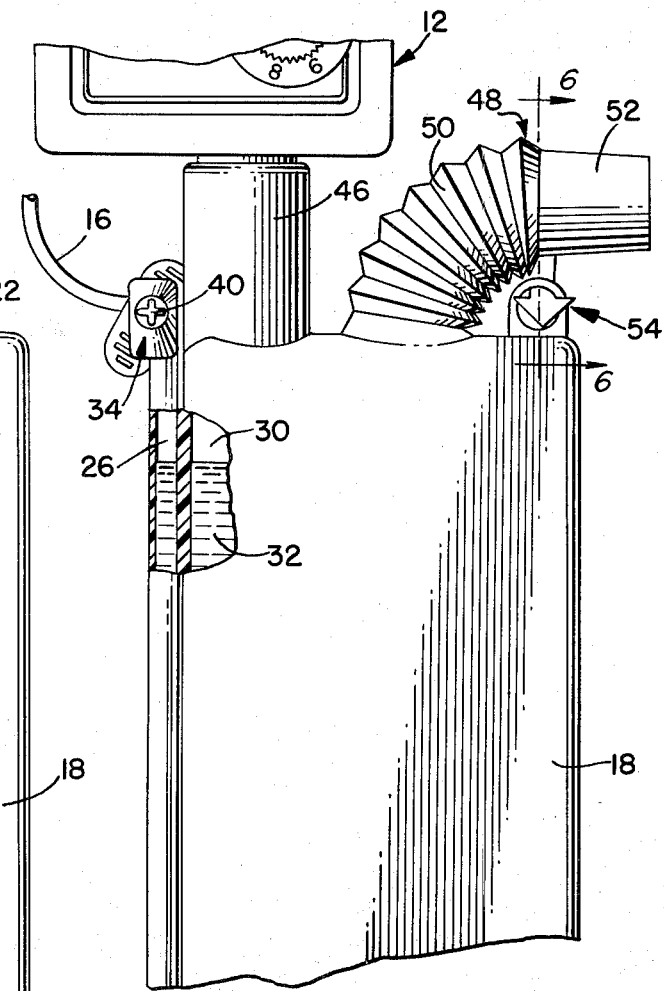
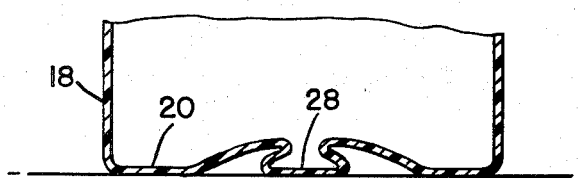

NEBULIZER BOTTLE

BACKGROUND OF INVENTION

This invention relates generally to liquid storing bottles of the blow molded, thermoplastic type adapted to be utilized as part of a nebulizing system for inhalation therapy purposes.

Thermoplastic, liquid storing bottles of the foregoing type are generally well known as disclosed in several prior patents owned by the Assignee of the present application, such as U.S. Pat. Nos. 3,903,216 and 4,187,951. Such bottle containers store liquid that is drawn from the bottom through a liquid feed passage separate from the liquid storing chamber to humidify oxygen gas in a nebulizing system. The top end wall of the container is provided with at least one tubular flow section from which the oxygen gas is delivered to a patient.

The molding of a thermoplastic bottle container that is adaptable for certain nebulizing systems and yet convenient for patient use, presents problems because of the flow passage coupling and flow directional requirements. It is, therefore, an important object of the present invention to provide a new and useful bottle container configuration which will be suitable for thermoplastic molding purposes and yet meet the special requirements of a nebulizing system.

Another object in accordance with the foregoing object is to provide a bottle container configuration which will facilitate its use for inhalation therapy as part of a nebulizing system.

SUMMARY OF THE INVENTION

In accordance with the present invention, the bottle container is provided with two parallel spaced tubular flow sections projecting from the top end wall and an enlargement of the liquid feed passage formation at its upper end adjacent to the top end wall to present a frangible side face through which a puncturing portion of a flexible conduct is inserted. One of the tubular flow sections is threaded to mount the nebulizing components such as a heater through which an oxygen mixture is introduced into the container. The other flow section has a corrugated portion enabling it to be bent to direct an outlet nozzle portion at right angles to the other inflow section for convenient reception of the discharge by a patient. The outlet flow section is held in its bent position by means of an arrow-shaped latch element projecting from the outlet nozzle portion and received through a loop type retainer element projecting from the top end wall of the container.

BRIEF DESCRIPTION OF DRAWING FIGURES

A specific embodiment of the invention is hereinafter described in greater detail with reference to the accompanying drawings, wherein:

FIG. 2 is a partial end elevation view of the apparatus shown in FIG. 1.

FIG. 3 is a partial side elevation view of the apparatus in an operative position.

FIG. 5 is a partial section view taken substantially through a plane indicated by section line 5—5 FIG. 1.

DETAILED DESCRIPTION OF PREFERRED EMBODIMENT

Figure 1:
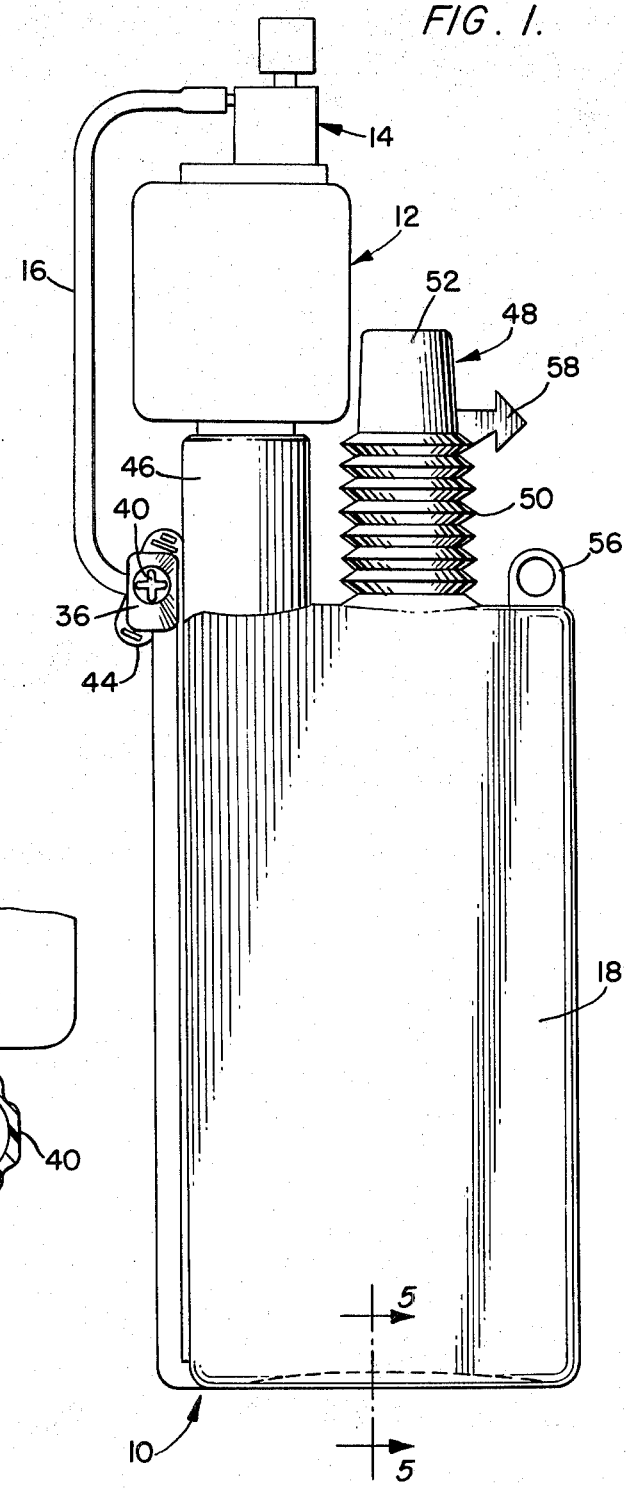
FIG. 1 is a side elevation view of a nebulizing apparatus with which the present invention is associated.

Referring now to the drawings in detail, a bottle container made of a thermoplastic material and generally referred to by reference numeral 10 is shown in FIGS. 1, 2, and 3. The bottle is formed by a blow molding technique well known in the art with liquid stored therein for inhalation therapy purposes. The bottle container itself is therefore formed from a unitary piece of molded material, and is adapted to be coupled in series to a heater 12 and vortex mixer 14 to which oxygen gas is fed. A flexible conduit 16 is coupled between the container and the mixer as shown in FIG. 1 to complete a nebulizing system with which the bottle is associated.

The bottle container 10 includes interconnected vertical side walls 18, a bottom wall 20 and atop end wall 22. Formed integrally with one of the side walls is a tubular formation 24 enclosing a liquid feed passage 26 as more clearly seen in FIG. 3. An intermediate support formation 28 is formed in the bottom wall as shown in FIG. 5 while two parallel spaced tubular flow sections 46 and 48 extend from the top end wall 22 as shown in FIG. 1. The passage 26 in the tubular formation 24 is in fluid communication adjacent to the bottom wall 20 with a fluid storing chamber 30 enclosed by the bottle container within which a body of liquid 32 is stored as shown in FIG. 3. The liquid is adapted to be drawn out of the chamber 30 through passage 26 into the flexible conduit 16. A coupling assembly generally referred to by reference numeral 34, couples the conduit 16 to the tubular formation 24 for this purpose.

Figure 4:
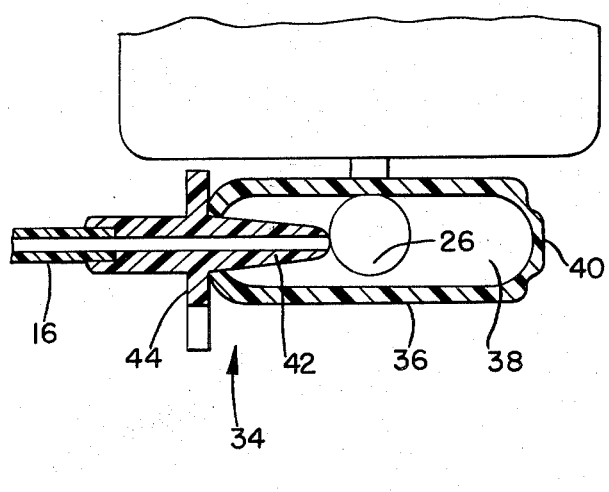
FIG. 4 is an enlarged partial section view taken substantially through a plane indicated by section line 4—4 in FIG. 2.

As more clearly seen in FIGS. 2 and 4, the coupling assembly 34 includes an enlarged portion 36 of the tubular formation 24 adjacent the top wall 22 enclosing a coupling chamber 38. A pair of parallel spaced frangible side faces 40 are formed on the enlarged portion 36 laterally of the passage 26. A pointed puncturing end portion 42 of the conduit 16 is adapted to be inserted through one of the frangible faces 40, as shown in FIG. 4 to establish fluid communication between the conduit 16 and passage 26. A sealing flange 44 is secured to the puncturing end portion for abutment with the punctured side face in order to seal the chamber 38. Thus, liquid will be drawn through conduit 16 from the container to the mixer 14 of the nebulizing system.

Figure 6:
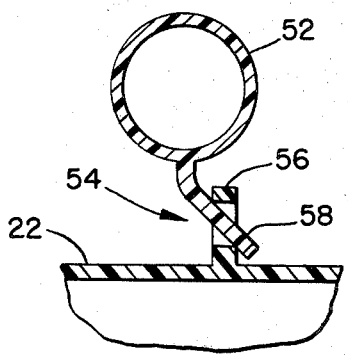
FIG. 6 is a partial section view taken substantially through a plane indicated by section line 6—6 in FIG. 3.

Oxygen mixed with water by mixer 14 and heated by heater 12 is fed to the upper gas space in the container through the tubular flow section 46 on which the heater is mounted by means of an externally threaded portion of flow section 46. The misted and heated oxygen is discharged from the other of the tubular flow sections 48 which ordinarily projects in one direction from the end wall 22 as shown in FIG. 1, parallel to flow section 46. Flow section 48 has, however, an elastically deformable corrugated portion 50 adjacent to the end wall 22 enabling the flow section to be angularly bent as shown in FIG. 3 so that a nozzle portion 52 of the flow section spaced from the end wall 22 may project perpendicular to flow section 46 for convenient inhalation of the discharge therefrom by the patient. Releasable holding means generally referred to by reference numeral 54 is provided to hold the flow section 48 in its operative position as shown in FIGS. 3 and 6.

The holding means 54 includes a retainer formation 56 in the form of a loop that is formed integral with and projects from end wall 22 of the container. A latch formation 58 having an arrow shape is inserted, when deformed, through the retainer loop formation 56. The latch formation is formed integral with and projects from the nozzle portion 52. The nozzle portion is thereby held in the operative position for patient inhalation therapy purposes.

What is claimed is:

1. In combination with a container having an end wall from which at least one tubular flow section extends in one direction and is bent to an operative position directing flow transversely of said one direction, the improvement residing in means for holding the tubular flow section in said operative position, comprising a retainer formation projecting from the end wall, and latch means projecting from the tubular flow section for reception through the retainer formation in the operative position of the tubular flow section.

2. The combination of claim 1 wherein said container, the tubular flow section and the holding means are all formed from a unitary piece of flexible material.

3. The improvement as defined in claim 2 wherein said retainer formation is a loop element.

4. The improvement as defined in claim 3 wherein said latch means is an elastically deformable arrow shaped element.

5. The combination of claim 4 wherein said tubular flow section includes a corrugated portion adjacent the end wall and a nozzle portion spaced from the end wall, said latch means projecting from the nozzle portion.

6. The improvement as defined in claim 1 wherein said retainer formation is a loop element.

7. The improvement as defined in claim 6 wherein said latch means is an elastically deformable arrow shaped element.

8. The combination of claim 1 wherein said tubular flow section includes a corrugated portion adjacent the end wall and a nozzle portion spaced from the end wall, said latch means projecting from the nozzle portion.

9. A unitary container adapted to be utilized for inhalation therapy, comprising interconnected side, bottom and top walls enclosing a liquid storing chamber, an elongated tubular formation secured to the side wall enclosing a passage in fluid communication with the chamber adjacent to the bottom wall, said tubular formation having a laterally enlarged portion adjacent the top wall enclosing a coupling chamber, at least one frangible face being formed on the enlarged portion generally parallel to the passage, and a pair of tubular flow sections extending from the top wall in substantially parallel spaced relation to each other, said tubular flow sections having a corrugated portion enabling displacement thereof to an operative position extending substantially perpendicular to the other of the tubular flow sections, holding means, said holding means having a retainer formation projecting from the top wall and latch means projecting from the tubular flow section for reception through the retaining formation in the operative position of said one of the tubular flow sections.

10. The combination of claim 9 including a conduit having a puncturing end portion insertable through the frangible face of the enlarged portion of the tubular formation into the coupling chamber, and a sealing flange adapted to abut the frangible face to seal the coupling chamber when the puncturing end portion is inserted therein.

* * * * *